(12) United States Patent
Cosmescu

(10) Patent No.: US 10,039,612 B2
(45) Date of Patent: Aug. 7, 2018

(54) LIGHT ATTACHMENT DEVICE FOR ELECTROSURGICAL PENCIL AND ELECTROSURGICAL PENCIL ATTACHMENTS

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 0 days.

(21) Appl. No.: 15/225,001

(22) Filed: Aug. 1, 2016

(65) Prior Publication Data

US 2016/0338796 A1 Nov. 24, 2016

Related U.S. Application Data

(63) Continuation of application No. 13/465,854, filed on May 7, 2012, now Pat. No. 9,554,867.

(60) Provisional application No. 61/483,609, filed on May 6, 2011, provisional application No. 61/489,895, filed on May 25, 2011.

(51) Int. Cl.
| | |
|---|---|
| *A61B 90/35* | (2016.01) |
| *A61B 18/14* | (2006.01) |
| *A61B 90/30* | (2016.01) |
| *A61B 17/00* | (2006.01) |

(52) U.S. Cl.
CPC .......... *A61B 90/35* (2016.02); *A61B 18/1402* (2013.01); *A61B 90/30* (2016.02); *A61B 2017/00734* (2013.01); *A61B 2090/309* (2016.02); *A61B 2560/0214* (2013.01); *A61B 2560/0418* (2013.01)

(58) Field of Classification Search
CPC ............ A61B 18/1402; A61B 19/5202; A61B 2017/00734; A61B 2019/521
See application file for complete search history.

(56) References Cited

U.S. PATENT DOCUMENTS

| | | | |
|---|---|---|---|
| 5,318,516 A | 6/1994 | Cosmescu | |
| 6,562,032 B1* | 5/2003 | Ellman | .......... A61B 17/320068 606/41 |
| 7,306,559 B2* | 12/2007 | Williams | ............... A61B 17/02 600/245 |
| 2002/0009275 A1 | 1/2002 | Williams et al. | |
| 2005/0143664 A1* | 6/2005 | Chen | .................... A61B 5/6852 600/478 |
| 2006/0291195 A1 | 12/2006 | Horrell et al. | |
| 2007/0049927 A1 | 3/2007 | Saltzman | |
| 2010/0125172 A1 | 5/2010 | Jayaraj | |

(Continued)

FOREIGN PATENT DOCUMENTS

| | | |
|---|---|---|
| CN | 102037784 A | 4/2011 |
| EP | 2027824 A1 | 2/2009 |
| JP | 11-226026 A | 8/1999 |

(Continued)

*Primary Examiner* — Amanda Patton
(74) *Attorney, Agent, or Firm* — Zeman-Mullen & Ford, LLP

(57) ABSTRACT

A light attachment device for removable attachment to an electrosurgical pencil and/or an electrosurgical pencil attachment such as a shroud for an electrosurgical pencil. The light attachment device may be automatically turned on and off in conjunction with the activation and deactivation of the electrosurgical pencil and/or electrosurgical pencil attachment.

18 Claims, 4 Drawing Sheets

(56) References Cited

U.S. PATENT DOCUMENTS

2011/0074304 A1   3/2011   Honsberg-Riedl et al.

FOREIGN PATENT DOCUMENTS

| JP | 2003-162904 A | 6/2003 |
| JP | 2009-050705 A | 3/2009 |

* cited by examiner

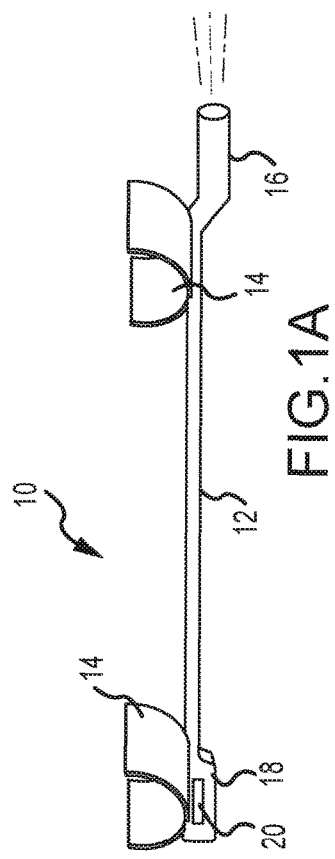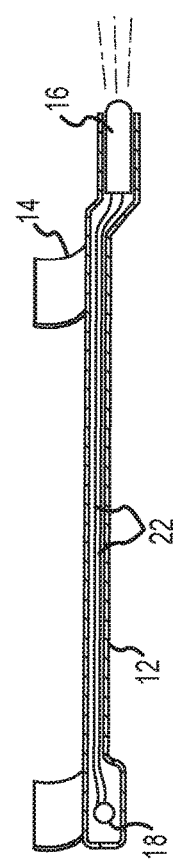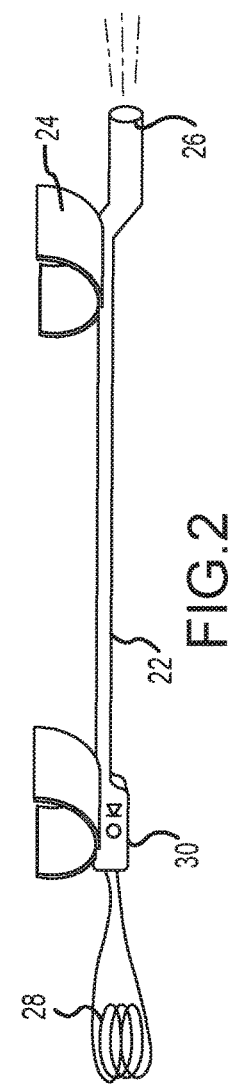

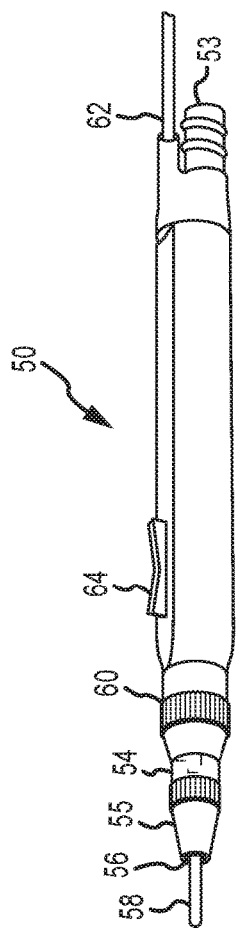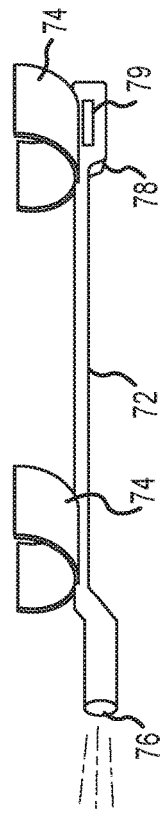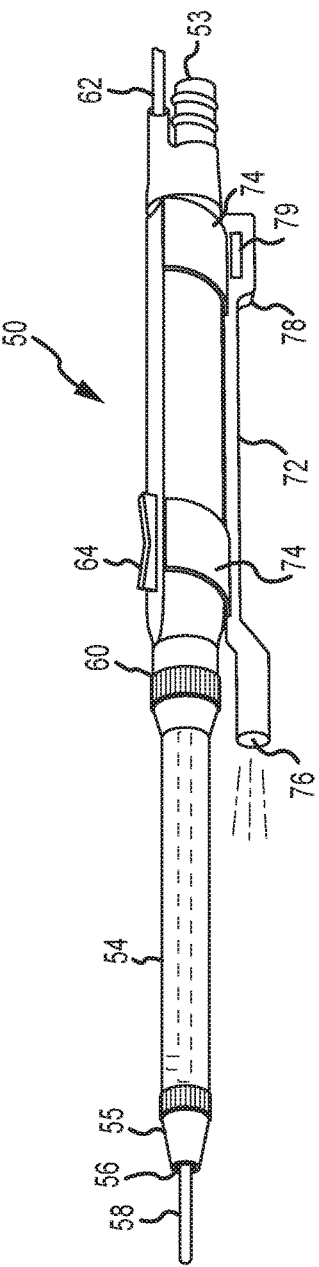

LIGHT ATTACHMENT DEVICE FOR ELECTROSURGICAL PENCIL AND ELECTROSURGICAL PENCIL ATTACHMENTS

CROSS-REFERENCE TO RELATED APPLICATIONS

This application is a continuation of and claims benefit of priority to U.S. Nonprovisional patent application Ser. No. 13/465,854 filed May 7, 2012, currently pending, which application claims the benefit of, and priority to, U.S. Provisional Application No. 61/483,609, filed May 6, 2011, and U.S. Provisional Patent Application No. 61/489,895, filed May 25, 2011 which applications are hereby incorporated by reference in their entireties.

FIELD OF INVENTION

The present invention generally relates to a light attachment device for an electrosurgery pencil and/or an electrosurgery pencil attachment device such as an electrosurgery shroud attachment device, for example. More particularly, the light attachment device of the present invention includes a support member, at least one attachment member connected to the support member for attaching the light attachment device to an electrosurgery pencil and/or an electrosurgery pencil attachment device, and at least one lighting element connected to the support member and/or the one or more attachment members.

BACKGROUND OF THE INVENTION

Most electrosurgery pencils now include smoke evacuation means to remove smoke, fluids, and debris away from the surgical site during a surgical procedure. However, although this removal of smoke, fluids, and debris provides a surgeon with better visibility during cutting and/or coagulation at the surgical site, some surgeries involve parts of the body that have less visibility than other parts of the body especially in those areas that are deeper in the body cavity. Further, although external lighting aids can be used that are separate and apart from the electrosurgery pencil, the use of such lighting aids is not efficient and may result in a more crowded surgical site thereby making manipulation of the electrosurgery pencil by the surgeon more difficult.

Accordingly, there is a need for a light attachment device for both electrosurgery pencils and electrosurgery pencil attachments that can be easily and removably secured to an electrosurgery pencil and/or electrosurgery pencil attachment so that the area of/in a patient's body where cutting and/or coagulation takes place can be illuminated. There is also a need for a light attachment device for electrosurgery pencils and electrosurgery pencil attachments that includes a movable lighting element that can be moved in all directions with respect to the light attachment device in order to better illuminate an area in or on a patient where an operation or medical procedure is taking place.

SUMMARY OF THE INVENTION

The present invention is directed to a light attachment device for any type of electrosurgical pencil or electrosurgical pencil attachment such as an electrosurgical pencil shroud attachment. The light attachment device can be set in any position in which the surgeon feels comfortable. The light attachment device of the present invention will improve the visibility at the surgical site by concentrating a beam of light at the electrode. The light may be an LED light that is powered by a battery located within the device. Activation is performed by a switch. Alternatively, the battery in the device may be replaced by an RF pick up coil which uses RF linkage for powering the LED. In this alternative embodiment using a pick up coil, when cutting or coagulation is performed by utilizing the electrosurgical pencil, the light or LED will come on when the cutting and/or coagulation of the electrosurgical pencil is activated and the light or LED will turn off when the cutting and/or coagulation of the electrosurgical pencil is deactivated.

Either of the above described embodiments of the device may also be used in conjunction with an electrosurgical attachment device such as an electrosurgical pencil shroud attachment. In this instance, the light attachment device of the present invention is connected to/attached to the electrosurgical pencil shroud attachment.

The light attachment device of the present invention may be attached to an electrosurgical pencil, a telescopic electrosurgical pencil, and/or any type of electrosurgical pencil attachment. In addition, the light attachment device of the present invention may itself be telescopic thereby allowing a user to extend or retract the light depending on the user's needs.

In one exemplary embodiment, the light attachment device of the present invention includes a support member, one or more attachment members connected to the support member for attaching the light attachment device to an electrosurgical pencil and/or an electrosurgical pencil attachment, and one or more lighting elements connected to the support member and/or the one or more attachment members. The one or more attachment members may have a generally open semi-circular shape so that at least a portion of an electrosurgical pencil and/or an electrosurgical pencil attachment can fit within the generally semi-circular shape of the attachment member. In another exemplary embodiment, the support member has two opposing ends and at least one lighting element is positioned near one opposing end and an element for powering the lighting element is positioned near the other opposing end of the support member. In addition, the light attachment device includes two attachment members connected to the support member with one attachment member positioned near the lighting element and the other attachment member positioned near element or powering the lighting element.

The lighting element in the light attachment device of the present invention may comprise any number of elements and variations. For, example, the lighting element may comprise one or more light emitting diodes (LEDs) and at least one battery for powering the one or more light emitting diodes. In another example, the lighting element may comprise one or more LEDs that are powered by a radio-frequency pick-up coil such as those radio-frequency pick-up coils known in the art. In still another example, the radio-frequency pick-up coil in the last example may comprise a battery-free radio frequency sensor on a flexible substrate. In addition, the lighting element may comprise a portion of and/or extend from the support member and the lighting element may be movable and/or bendable in any direction so that a surgeon can easily position the lighting element into the most effective position for improving the visibility of the surgical site.

The support member of the light attachment device of the present invention may have a top surface and a bottom surface with one or more attachment members extending beyond a top surface of the support member. Further, the one or more attachment members may function like clip members that can be removably secured to i) at least a portion of the bottom of an electrosurgical pencil and/or an electrosurgical pencil attachment and/or ii) at least a portion of the top of an electrosurgical pencil and/or an electrosurgical pencil attachment.

In still another exemplary embodiment, the light attachment device of the present invention may include a support member having a top surface and a bottom surface, one or more attachment members connected to the support member for attaching the light attachment device to an electrosurgery pencil and/or an electrosurgery pencil attachment, such as a shroud for smoke evacuation, and at least one lighting element connected to the support member and/or one or more of the attachment members. The lighting element may be powered by a battery-free radio frequency sensor contained on a flexible substrate where the flexible substrate also functions as an attachment member for attaching the light attachment device to an electrosurgery pencil and/or an electrosurgery pencil attachment. The flexible substrate may comprise a generally open semi-circular shape so that at least a portion of an electrosurgery pencil and/or an electrosurgery pencil attachment can fit within the semi-circular shape of the flexible substrate. In addition, the lighting element may be automatically turned on and off when the electosurgery pencil and/or an electrosurgery pencil attachment are respectively activated and deactivated.

BRIEF DESCRIPTION OF THE DRAWINGS

The subject invention will hereinafter be described in conjunction with the appended drawing figures, wherein like numerals denote like elements, and FIG. 1A is perspective side view of one exemplary embodiment of the light attachment device of the present invention;

FIG. 1B is a longitudinal cross sectional view of the exemplary embodiment of the light attachment device of the present invention shown in FIG. 1A;

FIG. 2 is a perspective view of another exemplary embodiment of the light attachment device of the present invention;

FIG. 3 is a perspective view of a prior art electrosurgery pencil;

FIG. 4 is a perspective view of another exemplary embodiment of the light attachment device of the present invention;

FIG. 5 is a perspective view of the exemplary embodiment of the light attachment device of the present invention shown in FIG. 4 shown attached to the prior art electrosurgery pencil shown in FIG. 3;

DETAILED DESCRIPTION

Figure 6:
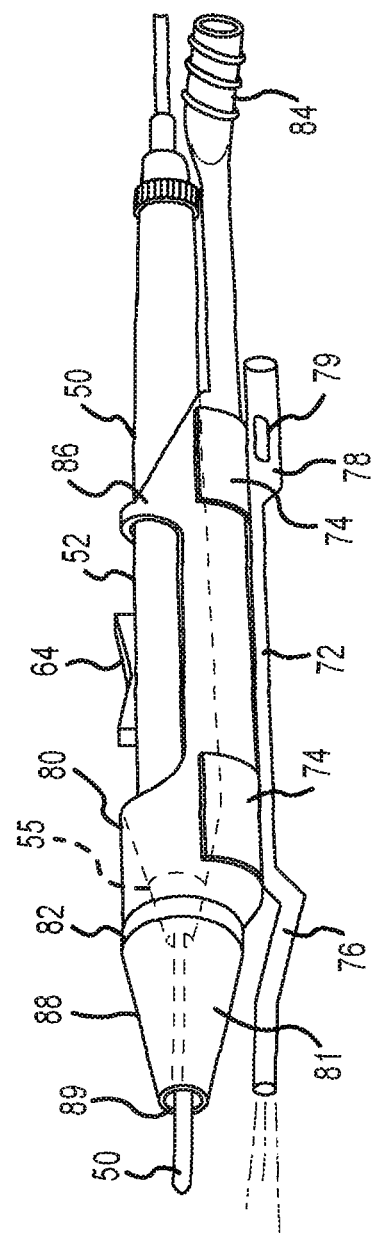
FIG. 6 is a perspective view of the exemplary embodiment of the light attachment device of the present invention shown in FIG. 4 shown attached to a prior art electrosurgery pencil shroud attachment which is in turn attached to a prior art electrosurgery pencil.

The present invention is generally directed to a light attachment device of an electrosurgical pencil and/or an electrosurgical pencil attachment. Examples of electrosurgery pencils and shrouds adapted to fit over electrosurgery pencils to which the light attachment device of the present invention may be attached can be seen in U.S. Pat. Nos. 6,142,995 and 7,112,199, both of which are herein incorporate by reference.

A perspective side view of one exemplary embodiment of the light attachment device 10 of the present invention is shown in FIG. 1. Light attachment device 10 includes a support member 12, one or more attachment members 14 connected to the support member 12 for attaching the light attachment device 10 to an electrosurgical pencil and/or an electrosurgical pencil attachment, and one or more lighting elements 16 connected to the support member 12 and/or the one or more attachment members 14. As shown in the embodiment depicted in FIG. 1, a diameter of the support member 12 is less than half the diameter of the one or more attachment members 14. The lighting element 16 may form a portion of and/or extend from the support member 12 and the lighting element 16 may be moveable and/or bendable in any direction so that a surgeon can easily position the lighting element into the most effective position for improving the visibility of the surgical site by connecting a beam of light at the electrode of the electrosurgical pencil. The lighting element 16 may comprise one or more light emitting diodes (LEDs) that are powered by a battery 18 located at an end of support member 12 that is opposite the lighting element 16. The light attachment device 10 may also include a switch 20 connected to battery 18 for turning the lighting element on and off. Alternatively, lighting element 16 may be turned on and off in conjunction with the activation and deactivation of an electrosurgical pencil and/or electrosurgical pencil attachment by including sensors in the light attachment device 10.

FIG. 1B shows a longitudinal cross sectional view of the exemplary embodiment of the light attachment device 10 of the present invention shown in FIG. 1A. As shown in FIG. 1B, lighting element 16 may be powered by battery 18 by connecting battery 18 to lighting element 16 via wires 22 which are contained within support element 12. As previously mentioned above, lighting element 16 may be set in any position that is comfortable to the surgeon so that the lighting element projects a beam of light at the site of electrode of the electrosurgical pencil.

A perspective view of another exemplary embodiment of the light attachment device 20 of the present invention is shown in FIG. 2. Light attachment device 20 includes a support member 22, one or more attachment members 24 connected to the support member 22 for attaching the light attachment device 20 to an electrosurgical pencil and/or an electrosurgical pencil attachment, and one or more lighting elements 26 connected to the support member 22 and/or the one or more attachment members 24. The lighting element 26 may form a portion of and/or extend from the support member 22 and the lighting element 26 may be movable and/or bendable in any direction so that a surgeon can easily position the lighting element into the most effective position for improving the visibility of the surgical site by concentrating a beam of light at the electrode of the electrosurgical pencil. The lighting element 26 may comprise one or more light emitting diodes (LEDs) that are powered by a radio-frequency pick-up coil 28 located at an end of support member 22 that is opposite the lighting element 26. Radio-frequency pick-up coil may be connected to a diode 30 which is in turn connected to lighting element 26. Lighting element 26 may be turned on and off in conjunction with the activation and deactivation of an electrosurgical pencil and/ or electrosurgical pencil attachment.

FIG. 3 is a perspective view of a prior art electrosurgery pencil 50. Electrosurgery pencil 50 is well known in the prior art and may include a hollow handpiece member 52 having a smoke evacuation end 53 for connecting the handpiece to a vacuum source, a hollow telescopic member 54 that fits concentrically within the hollow handpiece member 52 wherein the telescopic member has a nozzle 55 and a first end 56 through which electrode 58 extends, a locking member 60 for locking the telescopic member 54 in place with respect to the handpiece member 52, electrical means 62 for connecting the electrosurgery pencil to a power source, and switching means 64 for switching between cutting and coagulation.

FIG. 4 is a perspective view of another exemplary embodiment of the light attachment device 70 of the present invention. Light attachment device 70 includes a support member 72, one or more attachment members 74 connected to the support member 72 for attaching the light attachment device 70 to an electrosurgical pencil and/or an electrosurgical pencil attachment, and one or more lighting elements 76 connected to the support member 72 and/or the one or more attachment members 74. The one or more attachment members 74 may comprise a generally open semi-circular shape so that they may function as clips for attachment to an electrosurgery pencil and/or electrosurgery pencil attachment. The lighting element 76 may form a portion of and/or extend from the support member 72 and the lighting element 76 may be movable and/or bendable in any direction so that a surgeon can easily position the lighting element into the most effective position for improving the visibility of the surgical site by concentrating a beam of light at the electrode of the electrosurgical pencil. Lighting element 78 may be powered by any powering element 78 previously described above with reference to other alternative embodiments of the light attachment device of the present invention and light attachment device 10 may also include a switch 79 for turning the lighting element 76 on and off. Alternatively, lighting element 76 may be turned on and off in conjunction with the activation and deactivation of an electrosurgical pencil and/or electrosurgical pencil attachment.

FIG. 5 is a perspective view of the exemplary embodiment of the light attachment device 70 of the present invention shown in FIG. 4 shown attached to the prior art telescopic electrosurgery pencil 50 shown in FIG. 3 with the telescopic electrosurgical pencil 50 shown extended or telescoped. As shown in FIG. 5, the one or more attachment members 74 may comprise a generally open semi-circular shape that function to act like clips in removably attaching the light attachment device 70 of the present invention to at least a portion of the bottom of the telescopic electrosurgical pencil 50. It should also be understood by those skilled in the art that light attachment device 70 may also be telescopic and thereby further include two support members with one concentrically retained within the other so that one can telescope or extend outward (like the telescopic electrosurgery pencil) toward the electrode end of an electrosurgery pencil.

A perspective view of the exemplary embodiment of the light attachment device 70 of the present invention shown in FIG. 4 shown attached to a prior art electrosurgery pencil shroud attachment 80 which is in turn attached to a prior art electrosurgery pencil 50 is shown in FIG. 6. Prior art electrosurgical pencil shroud attachment 80 includes a conduit 81 having an open first end 82, an open second end 84, and a generally semi-circular shaped hollow interior, a handpiece holder 86 for removably receiving the electrosurgery pencil 50 formed continuously with at least a portion of a top outer surface of the conduit 81, a nozzle member 88 positioned near the first end 82 of the conduit 81 where the nozzle member 88 has a first open end 89 through which an electrode 58 from electrosurgery pencil 50 can extend. As shown in FIG. 6, the one or more attachment members 74 may comprise a generally open semi-circular shape that function to act like clips in removably attaching the light attachment device 70 of the present invention to at least a portion of the bottom of the electrosurgical pencil shroud attachment 80.

Figure 7:
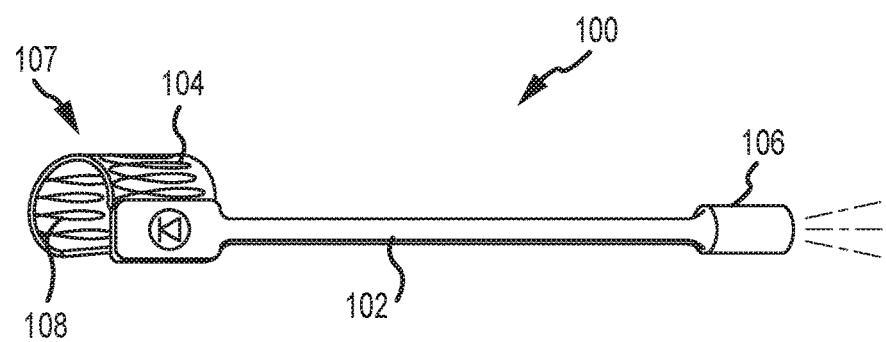
FIG. 7 is a perspective view of still another exemplary embodiment of the light attachment device of the present invention.

FIG. 7 is a perspective view of still another exemplary embodiment of the light attachment device 100 of the present invention. Light attachment device 100 includes a support member 102 having a top surface and a bottom surface, one or more attachment members 104 connected to the support member 102 for attaching the light attachment device 100 to an electrosurgery pencil and/or an electrosurgery pencil attachment, such as a shroud for smoke evacuation, and at least one lighting element 106 connected to the support member 102 and/or one or more of the attachment members 104. The lighting element 106 may be powered by a battery-free radio frequency sensor pick-up coil 107 contained on a flexible substrate 108 where the flexible substrate 108 also functions as an attachment member 104 for attaching the light attachment device 100 to an electrosurgery pencil and/or an electrosurgery pencil attachment. The flexible substrate 108 may comprise a generally open semi-circular shape so that at least a portion of an electrosurgery pencil and/or an electrosurgery pencil attachment can fit within the semi-circular shape of the flexible substrate. In addition, the lighting element 106 may be automatically turned on and off when the electrosurgery pencil and/or an electrosurgery pencil attachment are respectively activated and deactivated. Also, lighting element 106 may form a portion of and/or extend from the support member 102 and the lighting element 106 may be movable and/or bendable in any direction so that a surgeon can easily position the lighting element into the most effective position for improving the visibility of the surgical site by concentrating a beam of light at the electrode of the electrosurgical pencil.

The detailed description of exemplary embodiments of the invention herein shows various exemplary embodiments and the best modes, known to the inventor at this time, of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included figures are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

The invention claimed is:

1. A light attachment device for electrosurgical pencils and electrosurgical pencil attachments comprising:
   a support member;

at least two attachment members unconnected to one another but each connected to said support member for attaching the light attachment device to at least one of an electrosurgical pencil and an electrosurgical pencil attachment wherein a diameter of the rod-shaped support member is less than a half of a diameter of each of said at least two attachment members wherein each of said at least two attachment members extend above a surface of said support member without circumferentially containing any portion of the support member; and at least one lighting element connected to at least one of said support member and said at least one attachment member.

2. The light attachment device of claim 1 wherein said at least two attachment members have a generally semi-circular shape such that at least a portion of said at least one electrosurgical pencil and said electrosurgical pencil attachment can fit within the semi-circular shape of the attachment members.

3. The light attachment device of claim 1 wherein said at least one lighting element comprises at least one light emitting diode and at least one battery for powering the light emitting diode.

4. The light attachment device of claim 1 wherein said two attachment members each have a generally semi-circular shape.

5. The light attachment device of claim 1 wherein said at least one lighting element comprises at least one light emitting diode powered by a radio-frequency pick-up coil.

6. The light attachment device of claim 5 wherein said radio-frequency pick-up coil comprises a battery-free radio frequency sensor on a flexible substrate.

7. The light attachment device of claim 1 wherein said at least one lighting element is movable in relation to said support member.

8. The light attachment device of claim 7 wherein said at one least lighting element is capable of being moved in any direction.

9. The light attachment device of claim 1 wherein said support member has a top surface and a bottom surface and said at least two attachment members are connected to said top surface of said support member such that said at least two attachment members are removably secured to at least a portion of a bottom of said at least one of an electrosurgical pencil and an electrosurgical pencil attachment.

10. The light attachment device of claim 1 wherein one of said at least two attachment members is connected to an end of said support member opposite said at least one lighting element.

11. The light attachment device of claim 1 wherein said at least one lighting element is automatically turned on and off when at least one of an electrosurgery pencil and an electrosurgery pencil attachment are respectively activated and deactivated.

12. A light attachment device for electrosurgery pencils and electrosurgery pencil attachments comprising:
at least one of an electrosurgery pencil and an electrosurgery pencil attachment;
a support member;
at least one attachment member connected to said support member for attaching the light attachment device to at least one of the electrosurgery pencil and the electrosurgery pencil attachment wherein each of said at least one attachment member extends from a top surface of said support member without circumferentially containing any portion of the support member and said support member has a diameter less than a half of a diameter of said at least one attachment member; and
at least one lighting element connected to at least one of the support member and the at least one attachment member wherein said at least one lighting element is powered by a battery-free radio frequency sensor.

13. The light attachment device of claim 12 wherein said at least one lighting element is moveable in relation to said support member.

14. The light attachment device of claim 12 wherein said at least one attachment member has a generally semi-circular shape such that at least a portion of said at least one electrosurgical pencil and said electrosurgical pencil attachment can fit within the semi-circular shape of the attachment member.

15. The light attachment device of claim 14 wherein said at least one attachment member fits over at least a portion of a top of said at least one electrosurgical pencil and said electrosurgical pencil attachment.

16. The light attachment device of claim 14 wherein said at least one attachment member fits over at least a portion of a bottom of said at least one electrosurgical pencil and said electrosurgical pencil attachment.

17. The light attachment device of claim 12 wherein said at least one lighting element is automatically turned on and off when at least one of an electrosurgery pencil and an electrosurgery pencil attachment are respectively activated and deactivated.

18. The light attachment device of claim 12 wherein said at least one attachment member is flexible.

* * * * *